United States Patent
Carlsson et al.

(10) Patent No.: US 8,915,735 B1
(45) Date of Patent: Dec. 23, 2014

(54) ARRANGEMENT FOR OBTAINING RELIABLE ANCHORING OF A THREADED IMPLANT IN BONE

(75) Inventors: Lennart Carlsson, Mölndal (SE); Fredrik Engman, Mölnlycke (SE); Roger Fromell, Nödinge (SE); Lars Jörneus, Frillesås (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 0 days.

(21) Appl. No.: 09/509,869

(22) PCT Filed: Nov. 3, 1998

(86) PCT No.: PCT/SE98/01982
§ 371 (c)(1),
(2), (4) Date: Jun. 15, 2000

(87) PCT Pub. No.: WO99/23971
PCT Pub. Date: May 5, 1999

(30) Foreign Application Priority Data

Nov. 11, 1997 (SE) ...................................... 9704112

(51) Int. Cl.
*A61C 13/00* (2006.01)
(52) U.S. Cl.
USPC ............................. 433/174; 606/312; 606/315
(58) Field of Classification Search
CPC .. A61C 8/0022; A61C 8/0024; A61C 8/0025; A61B 17/86; A61B 17/8625
USPC ................. 606/304, 312, 317, 318, 309, 315; 433/172, 173, 174, 175, 176
See application file for complete search history.

(56) References Cited

U.S. PATENT DOCUMENTS

| 4,414,966 A | * | 11/1983 | Stednitz | ...................... 606/308 |
| 4,624,673 A | | 11/1986 | Meyer | |

(Continued)

FOREIGN PATENT DOCUMENTS

| DE | 4142584 | 6/1993 |
| EP | 0263809 | 4/1988 |

(Continued)

OTHER PUBLICATIONS

"Organ Der Deutschen Gesellschaft Fur Zahnarztliche Implantologie E.V.", Dgzi, 4, Orale Implantologie, p. 3 and p. 39.

(Continued)

*Primary Examiner* — Laura Bouchelle
(74) *Attorney, Agent, or Firm* — Walter Ottesen P.A.

(57) ABSTRACT

In an arrangement for obtaining reliable anchoring of a threaded implant (3) in dentine, a hole (2) is made in the bone substance. In the side wall (2b) of the hole it is possible to establish an internal threading which can cooperate with an external threading (3d) on the implant. The implant threading is arranged to force the bone substance out in essentially radial directions as a function of the extent to which the implant is screwed into the hole. The threading is arranged to effect greater forcing out of the bone substance at the outer parts of the hole than at the inner parts of the hole. The degree of forcing out is adapted in relation to the softness of the bone in order to achieve the reliable anchoring. Along at least part of the longitudinal direction of the implant, the implant threading can be given a non-circular configuration for the purpose of obtaining improved rotational stability in soft/weak bone. The implant can also have two or more thread spirals/thread entries which shorten the time for screwing the implant into the hole and additionally offer tight threading which permits effective integration with the bone substance during the healing-in process.

13 Claims, 4 Drawing Sheets

(56) References Cited

U.S. PATENT DOCUMENTS

| | | | |
|---|---|---|---|
| 4,713,003 | A | 12/1987 | Symington et al. |
| D296,362 | S | 6/1988 | Branemark |
| 4,863,383 | A | 9/1989 | Grafelmann |
| 5,064,425 | A | 11/1991 | Branemark et al. |
| 5,269,686 | A * | 12/1993 | James .................. 433/174 |
| 5,427,527 | A * | 6/1995 | Niznick et al. ............ 433/174 |
| 5,527,183 | A * | 6/1996 | O'Brien .................. 433/174 |
| 5,591,029 | A | 1/1997 | Zuest |
| 5,620,323 | A * | 4/1997 | Bressman et al. ........... 433/174 |
| 5,902,109 | A * | 5/1999 | Reams et al. ............. 433/174 |
| 2002/0182560 | A1 | 12/2002 | Park et al. |

FOREIGN PATENT DOCUMENTS

| | | |
|---|---|---|
| EP | 0282789 | 9/1988 |
| EP | 0424734 | 5/1991 |
| EP | 0530160 | 3/1993 |
| EP | 0641549 | 3/1995 |
| SE | 963091-1 | 10/1998 |
| WO | WO-83/02555 | 8/1983 |
| WO | 9306786 | 4/1993 |
| WO | 9407428 | 4/1994 |
| WO | 9725933 | 7/1997 |

OTHER PUBLICATIONS

Restorative Dentist's Manual, Branemark System, 015, "The Treatment of the Edentulous Jaw".

Nobel Biocare, Branemark System, "Implant Placement Procedure", MK, IV 04 MM RP Implant, Drilling Procedure for MK IV 04 MM RP Implant, pp. 39-40, Nobel Biocare AB, Box 5190, SE-402 26 Goteborg, Sweden., www.Nobelbiocare.com.

Van Nostrand'S Scientific Encyclopedia, D.Van Nostrand Company Inc., Princeton, New Jersey, Third Edition, 017, Screw Propeller—Scrotum, p. 1468.

TMS Link/TMS Link Plus, "Retention Pins, for Permanent Retention in the Most Demanding Indications", Coltene Whaledent, TMS Link/TMS Link Plus: "It's the Details That Make the Difference", TMS Link/TMS Link Plus: "For Various Indications in Anterior and Posterior Teeth", Comprehensive: "Four Pin Sizes Each With a Corresponding Kodex Drill".

Per Astrand, et al., Tapered Implants in Jaws With Soft Bone Quality: A Clinical and Radiographic 1-Year Study of the Branemark System Mark IV Fixture, pp. 213-218.

Bertil Friberg, et al., "One-Year Prospective Three-Center Study Comparing the Outcome of a "Soft Bone Implant" (Prototype MK IV) and the Standard Branemark Implant", pp. 71-77, 2003, BC Decker Inc.

Caroline McCarthy, et al, "Sinus Augmentation Bone Grafdts for the Provision of Dental Implants: Report of Clinical Outcome", The International Journal of Oral & Maxillofacial Implants, pp. 377-382, vol. 18, No. 3, 2003.

Leonardo Vanden Bogaerde, et al., "Early Function of Splinted Implants in Maxillas and Posterior Mandibles Using Branemark System, Machined-Surface Implants: An 18-Month Prospective Clinical Multicenter Study", pp. 21-28, Clinical Implant Dentistry and Related Research, vol. 5, Supplement 1, 2003.

Roland Glauser, et al, "Immediate Occlusal Loading of Branemark Tiunite™ Implants Placed Predominantly in Soft Bone: 1-Year Results of a Prospective Clinical Study", pp. 47-56, 2003, BC Decker Inc.

Morgan Ollssom, et al., "Early Loading of Maxillary Fixed Cross-Arch Dental Prostheses Supported by Six or Eight Oxidized Titanium Implants: Results After 1 Year of Loading, Case Series", pp. 81-87, 2003 BC Decker Inc., Clinical Implant Denistry and Related Research, vol. 5, Supplement 1, 2003.

Roland Glauser, et al., "Initial Implant Stability Using Different Implant Designs and Surgical Techniques." A Comparative Clinical Study Using Insertion Torque and Resonance Frequency Analysis, University of Zurich, Dental School, Switzerland, Dept of Biomaterials/Handicap Research, University if Gothenburg, Sweden, pp. 6-8, Applied Osseointegration Research, vol. 2, No. 1, 2001, 02 8375.

Katsuhiro Horiuchi, et al., "Anteroinferior Distraction of the Atrophic Subtotal Maxillary Alveolus for Implant Placement: A Case Report", pp. 416-423, vol. 17, No. 3, 2002.

M. Tomatis, et al., "Immediate Loading of Branemark Implants With Two Different Surfaces", Private Practice, Bologna Italy, Nobel Biocare AB, Gothenburg, Sweden, #78.

Guido Heydecke, et al., "Evolution and Use of Aluminum Oxide Single-Tooth Implant Abutments: A Short Review and Presentation of Two Cases", pp. 488-493, The International Journal of Prosthodontics, vol. 15, No. 5, 2002.

Thomas J. Balshi, et al., "Immediate Loading of Dental Implamts in the Edentulous Maxilla: Case Study of a Unique Protocal", pp. 37-46, vol. 23, No. 1, 2003, 03 8985.

Paulo Malo, et al., "A Pilot Study of Complete Edentulous Rehabilitation With Immediate Function Using a New Implant Design: Case Series", p. 223- 232, Clinical Implant Dentistry and Research, vol. 8, No. 4, 2006.

B. Al-Nawas, et al., "Comparative Histomorphometry and Resonance Frequency Analysis of Implants With Moderately Rough Surfaces in a Loaded Animal Model", pp. 1-8, The Authors Journal Compilation 2007 Blackwell Munksgaard.

Paul P. Lang, et al., "Maxillary Zirconia Implant Fixed Partial Dentures Opposing an Acrylic Resin Implant Fixed Complete Denture: A Two-Year Clinical Report", pp. 321-330, The Journal of Prosthetic Dentistry, vol. 97, Issue 6.

Morgan Ollsom, et al., "Early Loading of Maxillary Fixed Cross-Arch Dental Prostheses Supported by Six or Eight Oxidized Titanium Implants: Results After 1 Year of Loading, Case Series", pp. 81-87, 2003 BC Decker Inc., Clinical Implant Denistry and Related Research, vol. 5, Supplement 1, 2003

Antonio Rocci, et al., "Histology of Retrieved Immediately and Early Loaded Oxidized Implants: Light Microscopic Observations After 5 to 9 Months of Loading in the Posterior Mandibile", pp. 88-98, 2003 BC Decker Inc., Clinical Implant Dentistry and Related Research, vol. 5, Supplement 1, 2003.

Roland Glauser, et al, "Immediate Occlusal Loading of Branemark MKIV Tiunite™ Impplants Placed in Bone Quality Type 4", Universtiy of Zurich, Dental School, Switzerland, Department of Biomaterials, Institute of Surgical Sciences, Goteborg University, Gothenburg, Sweden, pp. 22 and 24, Applied Osseointegration Research, vol. 3, Nov. 1, 2002.

Dominic O'Sullivan, et al., "Measurements Comparing the Initial Stability of Five Designs of Dental Implants: A Human Cadaver Study", pp. 85-92, 2000 B.C. Decker Inc., Clinical Implant Dentistry and Related Research, vol. 2, No. 1, 2000.

49, Jovanovic SA, et al. "Sinus Bone Grafts With Tapered Machined Surfaced Titanium (MK IV) Dental Implants: 1-Year Clinical Follow-Up", Clinical Oral Implant., Res. 12, 2001, vol. 405, p. 393

Philippe Adriaenssens, et al., "Immediate Implant Function in the Anterior Maxilla: A Surgical Technique to Enhance Primary Stability for Branemark MK III and MK IV Implants", A Randomised, Prospective Clinical Study at the 1-Year Follow-Up, pp. 17-21, Applied Osseontegration Research, vol. 2, No. 1, 2001.

Antonio Rocci, et al., "Immediate Function of Single and Partial Reconstructions in the Maxilla Using MK IV Fixtures", A Retrospective Analysis, pp. 22-26, Applied Osseointegration Research, vol. 2, No. 1, 2001.

* cited by examiner

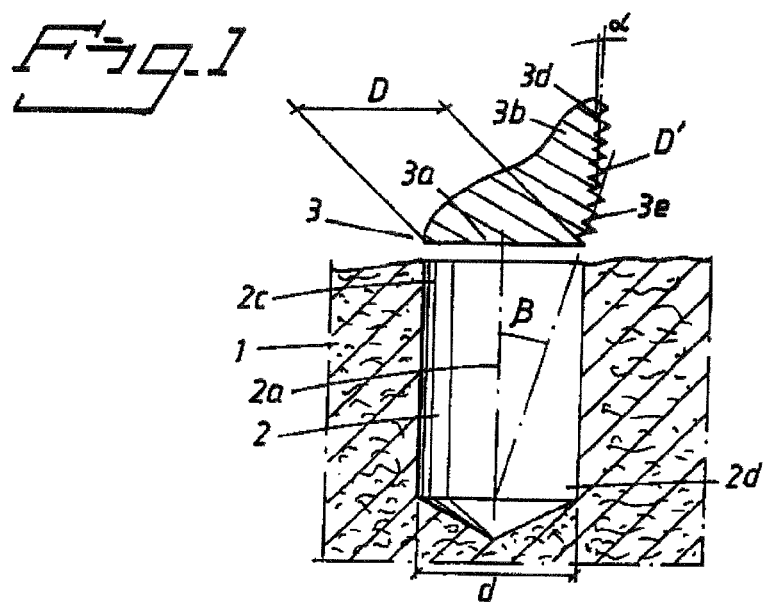
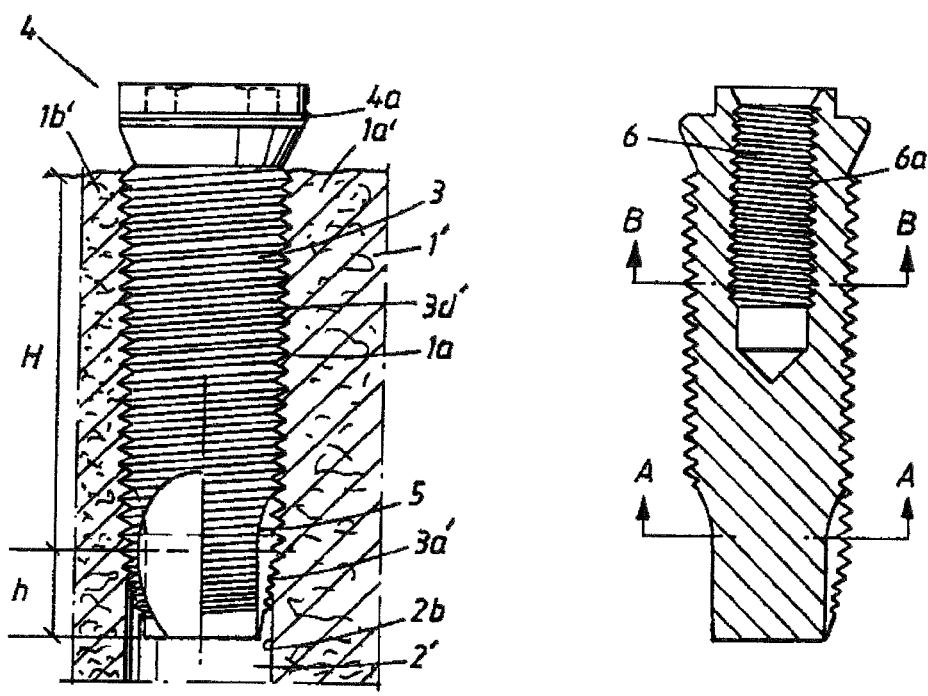

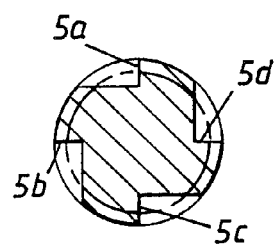
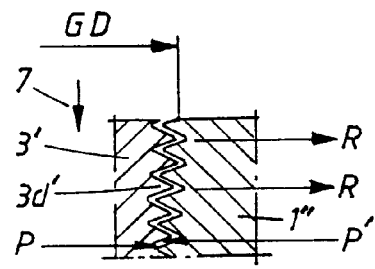
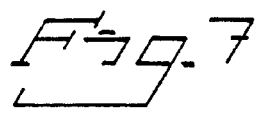
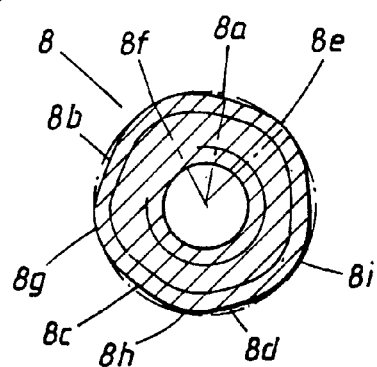
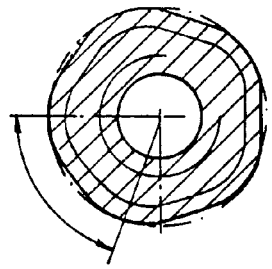
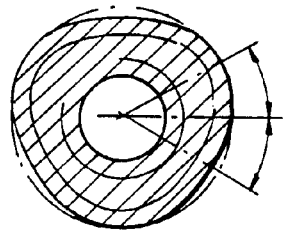
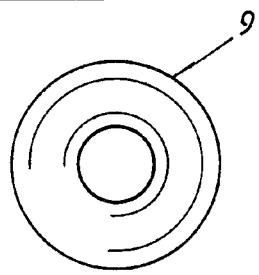

US 8,915,735 B1

ARRANGEMENT FOR OBTAINING RELIABLE ANCHORING OF A THREADED IMPLANT IN BONE

TECHNICAL FIELD

The present invention relates to an arrangement for obtaining reliable anchoring of a threaded implant in bone, preferably dentine, in the human body. The bone in question is in this case provided with a hole in whose side wall it is possible to establish an internal threading which can cooperate with an external threading on the implant for reliable anchoring and healing-in of the implant in the bone substance.

PRIOR ART

Implants with threads, for example self-tapping threads, for insertion/screwing into holes made in the bone/dentine are available in large numbers and designs on the open market and are described in the patent literature. Thus, for example, reference may be made to Swedish Patent Application 9603091-7 filed by the same Applicant filing the present patent application.

In this connection it is known to use different thread formations on implants. Thus, for example, it is already known to use implants with cone-shaped threads and to choose different conicities on one and the same implant. The methods for forming the holes in the bone/dentine are also already well known. In this connection, reference may be made, in purely general terms, to dental treatment by the Brånemark System®.

Some of the threaded implants are cylindrical, while others can have the said conical designs in order to imitate the tooth root which they are intended to replace. The implants are inserted into holes that have been drilled beforehand in the jaw bone. A cylindrical hole is drilled for cylindrical implants, and for conical implants a conical hole is prepared. The cited method using the Brånemark System® involves securing screw-shaped implants in the jaw bone. After a period of healing-in, normally about 3-6 months, the bone has grown in direct contact with the implant and the latter can then be used to support a prosthetic reconstruction. This is in most cases achieved by means of a so-called spacer element being attached to the implant, which can be done by a screw connection. A transfer cap is then attached to the top of the spacer upon so-called impression-taking, and the finished prosthetic reconstruction can thereafter be applied to the spacer.

From the known methods it is already known that good long-term results are obtained if the osteointegration between the bone and the implant can take place with a tight profile and small pitch of the threads in question. During the osteointegration, the bone tissue grows in direct contact with the implant. Upon fitting the implants, the said holes are drilled in the bone with great precision. In this connection it is already known to use tightening instruments which rotate at about 20-25 rpm.

In WO 97/25933 (PCT/US97/00332) it has already been proposed, especially in connection with hard dentine, that the body presenting the thread should be made non-circular (asymmetric) in its cross-section.

The purpose of the non-circularity is to reduce the friction between bone and implant on insertion of the implant. This is important mainly in the case of hard bone.

DESCRIPTION OF THE INVENTION

Technical Problem

The problem with using cylindrical implants in cylindrical holes is that the thread which is in most cases created by the self-tapping tip of the implant is worn away as the implant is screwed in, and with this wearing the thread is widened, mainly at the inlet/mouth of the hole in the bone. This results in the implant having a slightly loose anchoring, especially in weak/soft bone, which means that the implant has a poor initial stability. When using conical implants with a conical preparation, one of the greatest problems is the development of heat which occurs during the conical preparation. Since a conical drill cuts along the whole periphery, relatively great heat is generated, and this negative effect is amplified further by the fact that the cutting geometry of a conical drill becomes worse because a low surface pressure occurs at the periphery of the conical drill. This means that the drill cannot cut proper chips but instead scrapes bone away, and this has a high heat-generating effect. This heat can damage the bone and can lead to the bone nearest the drilled hole dying. This drastically reduces the possibilities of successful osteointegration. The object of the present invention is to solve the above problems among others.

The said use of a screw connection on the implant involves the screwing and unscrewing of screws. This represents a relatively great risk since the implant is subjected to breaking stresses which mean that the implant is at risk of being turned out of its position. This applies in particular if the implants are fitted in bone which is of weak/soft quality. The above unscrewing problems are especially pronounced in the case of implants with a thread which is circularly symmetrical. In most threaded implants, it is of course possible to arrange cutouts at the tip, which are intended both to cut threads and to contribute to the rotational stability. There are also implants with transverse holes for bone to grow into. A common feature of these known constructions is that the recesses and holes are relatively small when seen in relation to the threaded area of the implant. Since the surface of the recesses or holes is small, deformation or break-up of the ingrown bone can easily take place upon torsional loading. In addition, the holes and recesses are situated at the very front of the tip where in most cases the quality of the bone (its hardness) is poor. There is also an inherent weakness in that the holes and recesses reduce the threaded area of the implant. It must be emphasized here that it is essential to have the greatest possible threaded area for effective transfer of the functional load from the tooth prosthesis or tooth bridge down to the bone. This applies in particular in the case of soft bone.

Another problem with the known implants is that the respective implant, especially in the case of weak/soft bone quality, does not sit with sufficient stability in the bone directly after insertion. When this is the case, microscopic movements can occur between the implant and the surrounding bone tissue, for example when the bone is bent, which can happen when the bone is exposed to mastication loads or when the patient has a conventional tooth prosthesis which presses on the gum above the implant. It is then important for the implant to have sufficient initial stability. Previously known solutions have consisted in introducing changes to the surface, for example using a coating of hydroxyapatite or increasing the surface roughness of the implant and in this way offering increased initial stability and possibly better incorporation of the surrounding bone. A great disadvantage of the proposed solutions has been that it is not possible to predict the long-term success of the implant. There are various scientific articles which have been published concerning the poor long-term results of implants with a rough surface or with coatings.

An important precondition for being able to implement the abovementioned methods is to create the conditions for obtaining direct bone contact with the implant during the healing-in process. It is essential in this connection to perform meticulous surgery when fitting the implants. The hole for the implant must be drilled with great precision and in this connection it is of the utmost importance that the temperature in the bone does not become too high. These requirements have hitherto meant that both the drilling and the fitting of the implant have been carried out with the hole-forming and tightening instruments being operated at low speed. The speed of rotation which is normally employed when fitting implants is 20-25 rpm. This means that the time required for fitting an implant can amount to 1 minute or more. During this time, it is necessary for the surgeon fitting the implant to keep a very steady hand so as to ensure that the fine bone trabeculae surrounding the hole are not deformed or broken up. Wobbling movements of the instrument during tightening pose risks of deformation and break-up. Attempts have been made to solve this problem by providing the implant with an increased thread pitch. Normally, this means that the thread profile is greater and the thread becomes thinner. This thinner thread is disadvantageous in several respects. There are fewer threads and thus an increased stress concentration around each thread crest and also, with a coarser thread profile, a greater difference between the external and internal diameters, which for a given external diameter of the implant leads to a mechanically weaker implant. An alternative solution to this problem would be to increase the speed of the tightening instrument so that the implant rotates more quickly into position. This method also has disadvantages. The temperature of the bone tissue can become too high. Another factor to be taken into consideration is that a large number of the drilling and tightening instruments available on the market work at a speed which is limited to 20-25 rpm.

The invention is intended to solve the last-mentioned problems too.

Solution

The main characteristic of an arrangement according to the invention is that it satisfies one or a combination of two or all of the following features:
a) the implant threading is arranged, particularly in the case of soft bone substance, to force the bone substance out in essentially radial directions as a function of the extent to which the implant is screwed into the hole, the implant threading is arranged to effect greater forcing out of the bone substance at the outer parts of the hole than at the inner parts of the hole, and the degree of forcing out is adapted in relation to the softness of the bone substance in order to achieve the reliable anchoring,
b) along at least part of the longitudinal direction of the implant, the implant threading is given a non-circular or eccentric configuration for the purpose of obtaining improved rotational stability in soft/weak bone,
c) the implant is provided with a threading which comprises one or more portions with two or more thread spirals or thread entries which, despite shortening the time for screwing the implant into the hole, provide a tight threading which permits effective integration with the bone substance during the healing-in process/osteointegration.

In embodiments according to a) above, the implant threading is arranged to ensure that the pressure between the bone substance and the implant has essentially a constant or only slightly increasing value during the greater part of the operation of screwing the implant in. The implant threading can also comprise a portion whose thread has a slight conical narrowing towards the free end or tip of the implant and extends along at least the greater part of the length of the implant. In one embodiment, the front portion or tip of the implant can be designed with a conical thread which has a stronger conicity than the other thread or thread parts of the implant. The conicity measured over the diameter of the slightly conical thread can be chosen within the range of 0.1 to 0.4 mm or can have an angle of inclination of about 0.5-2°. The thread conicity of the thread of the portion or tip can be of the order of 0.4-0.8 mm or can be designed with an angle of inclination of about 10-15°. The tip can have a length which is 10-30% of the length of the total thread of the implant. In a preferred embodiment, an implant with slight conicity of the main part of its thread is used in a circular cylindrical hole in the bone.

In connection with the features according to b) above, the non-circularity or eccentricity is intended to substantially increase the rotational stability of the implant in the recently inserted (initial) state or the incorporated state of the implant. The non-circularity or eccentricity can also be provided to counteract the breaking up of the thread at the inner parts of the hole. In one embodiment, the implant is arranged with a minimum diameter or cross-sectional width which corresponds to or is only slightly greater, for example 1-5% greater, than the diameter of the hole in the bone/dentine. The minimum diameter of the implant is understood to mean the root diameter of the thread at the minimum diameter of the slightly conical portion. The tip or free end of the implant has a circular or concentric thread which, seen from the free end, merges gradually into a non-circular or eccentric thread on the remaining part or parts of the implant. The non-circularity is provided to ensure that there are no sharp corners, but only bevelled corners. The non-circularity can also be provided so that areas of maximum diameter are displaced in the peripheral direction from one thread turn to the next thread turn. The non-circularity can be provided on the thread-supporting body and/or on the outer portion of each thread.

Embodiments according to c) hereinabove can consist in the arrangement being intended to counteract deformation or breaking-up of free bone trabeculae which surround the hole in the bone. Further features of embodiments can be that the number of thread spirals can be chosen as a function of the desired time for screwing the implant into the hole and thus, for example, the number of thread spirals can be two, three or four. Further features of embodiments are that the number of thread spirals is adapted to the number of cutting edges on the implant so that symmetrical cutting forces are obtained.

Advantages

By means of what has been proposed above, implants are obtained which have very good properties. The implant can be provided with substantially improved starting properties, which mean that the implant easily "takes threads", even if the initial hole made in the bone is small in relation to the diameter of the implant. Because the pressure between the implant and the thread in the bone does not fall, this permits a gradually increasing advancing force which counteracts any tendency towards breaking the sometimes brittle threads in the bone. The initial stability of the implant in the hole can be improved since the elasticity of the bone means that the bone tissue can completely or partially spring back into the shallower portions of the fixture. After healing in, when new and in most cases stronger bone has grown in direct contact with the implant, the latter sits with great rotational stability since when slackening the implant it is necessary to break apart large areas of bone seen in relation to the total surface of the implant. This is important in particular in the case of soft bone. The implant thread can be designed with cross sections which are shaped as polygons, preferably with rounded corners, or with 3-sided, 5-sided or 7-sided geometry. This type of non-circular geometry has the property that it has an apparently considerably constant diameter when measured by sliding calliper or micrometer. To improve the starting properties of the implant, so that the implant easily takes threads at the start of screwing in, the implant can be provided with thread cutters. These can be arranged so that they cut at the greatest diameter of the implant, which can be expedient when the implant is conical and the conicity affords a clamping effect.

It is particularly important in the case of soft bone to combine non-circularity with conicity. This conicity can be such that the base diameter gradually increases, or, alternatively, the non-circularity increases in conjunction with a constant or only slightly increasing "internal diameter". The combination of non-circularity and conicity means that because of the pressure between bone tissue and implant the bone springs into the shallower parts of the implant. Non-circular cylindrical implants, by contrast, have a reduced pressure and reduced initial stability in soft bone because the pressure and resilience decrease.

With the aid of multiple thread entries, the pitch can be increased and, in this way, the time for tightening the implant can be shortened. Thus, by means of the invention, it is possible to obtain good initial stability and good gripping upon fitting. It is also possible to obtain more rapid fitting and less risk of wobble. In addition, it is possible to obtain a better secondary stability.

DESCRIPTION OF THE FIGURES

A presently proposed embodiment of an arrangement having the characteristic features of the invention will be described below with reference to the attached drawings, in which:

FIG. 1 shows, in vertical section, parts of a bone (dentine) with a circular hole made in it, and an implant which can be screwed into the circular hole, with conical threads with slight inclination, FIG. 2 shows, in vertical section, an implant applied in a circular hole in bone/dentine, shown partially, FIG. 3 shows, in vertical section, the implant according to FIG. 2 in a design embodiment, FIG. 4 shows a cross-section A-A of the implant tip according to FIG. 3, FIG. 5 shows, in a vertical view, parts of the thread interaction between an implant and bone/dentine, FIGS. 6 to 9 show cross-sections and an end view of an implant with non-circular cross-section.

DETAILED EMBODIMENT

Figure 10:
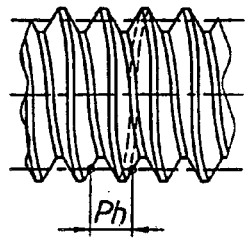
FIGS. 10 to 12 show implant threads with different multiple entries which give different thread pitches.

In FIG. 1, reference number 1 designates dentine. A circular hole 2 has been made in the dentine. The hole can be made in a manner known per se using equipment known per se. An implant with threads of different conicities can be applied to the hole. Parts of the said implant are represented by parts of the free end 3 of the implant. The said free end has a tip part 3a which merges into a part 3b. The latter part has a thread 3d which has a slight conicity. Slight conicity is understood here as meaning conicities in which an angle of inclination α is of the order of 1° in relation to a vertical axis 2a of the hole 2 or an axis parallel to this axis. The tip 3a is provided with a thread 3e which is arranged with a conicity which gives an angle β of the order of 10°. The entry surface or entry part of the tip 3a has a diameter D' which essentially corresponds to the diameter d of the hole or slightly exceeds the said diameter d. The hole diameter d can also be chosen as a function of the softness of the bone (quality). The upper and lower parts of the hole are indicated by 2c and 2d.

FIG. 2 shows a structural design of the implant 3 with associated thread 3d'. Here, the implant has been screwed fully into the hole 2' in the dentine and, on being screwed in, has created a thread 1a in the wall 5 of the hole in the dentine or the side wall 2b of the hole 2'. At its upper part, the implant has securing members/spacer members 4 for a special tooth replacement, tooth prosthesis, etc. (not shown). The member 4 can be provided with a flange 4a with which it is possible to define the final degree of threading of the implant so that optimum thread is exposed to the dentine. As can be seen from FIG. 2, the implant is in this case provided with cutting edges 5, of a type known per se, at the tip 3a'. The tip part 3a' has h which represents 20-30% of the total height H of the threaded part of the implant. By means of the conicity, an improved initial stability is obtained through compression 1a', 1b' of the bone.

FIG. 3 shows the implant according to FIG. 2 in vertical section. In this figure, a threaded recess 6 is shown whose internal thread has been labelled 6a. The said spacer arrangement 4 according to FIG. 2 can be screwed into the said internal thread in a manner known per se.

FIG. 4 shows that, at the said free end, the implant according to FIGS. 2 and 3 is designed with cutting edges known per se, which in FIG. 4 have been labelled 5a, 5b, 5c and 5d.

FIG. 5 (like FIG. 2, cf. 1a, 1b) shows that the chosen conicity for the thread 3d' (cf. FIG. 1) pushes the dentine substance 1" out in radial directions R. The conicity of the thread 3d' and the thread diameter GD of the inclined thread are in this case chosen such that the contact pressure P, P' is of essentially the same order or only slightly increases as the implant 3' is being screwed in a direction 7 into the dentine 1" (the hole made in it).

In accordance with the invention, the thread 3d/3d' according to the above can be designed with a non-circular/eccentric thread cross-section and/or with a non-circular cross-section for the thread-bearing body. FIGS. 6, 7 and 8 show different types of non-circularity and positions of rotation of the various thread cross-sections. The individual thread cross-sections can also have different non-circularity. In accordance with FIG. 9, the thread at the tip or free end of the implant can have a circular or concentric thread cross-section which at the top merges into a non-circular thread cross-section according to FIGS. 6-8. In this way it is possible to achieve a considerable freedom from wobble during tightening. In FIG. 6, one thread is indicated by 8. The thread has a number of depressions 8a, 8b, 8c and 8d. The parts effecting the threads in the dentine with the greatest radial dimensions are indicated by 8e, 8f, 8g, 8h and 8i. The characteristic of these protruding parts is that they do not have sharp corners, i.e. they have parts which are arcuate in cross-section. This applies also in the case of a non-circular thread-bearing body. The number of protrusions and depressions can vary from that indicated in FIG. 6, cf. FIGS. 7 and 8. FIG. 9 shows the case in which the implant has a circular or concentric thread 9 at the tip.

Figure 11:
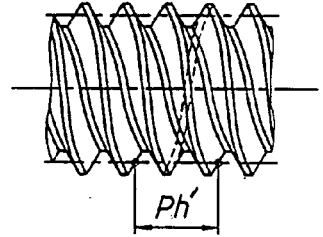
Figure 12:
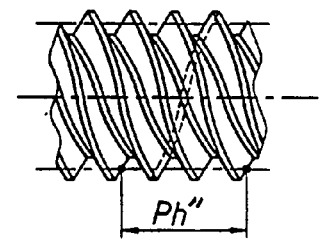

FIGS. 11 and 12 are intended to show so-called multiple thread entries or multiple thread spirals which, depending on the number of entries and spirals, provide different pitches, compare with FIG. 10 which shows a design with a single thread entry and thread spiral. FIG. 11 shows an embodiment with two thread entries or thread spirals which provide a pitch indicated by Ph', compare with the pitch Ph in FIG. 10. As the principle of double thread spirals is already well known per se, it will not be described in detail here. The principle is already known from completely different areas and for solving completely different problems. In this connection reference may be made to worm gears which use worm screws with multiple thread entries or thread spirals. FIG. 12 shows an embodiment with three thread entries or thread spirals which provide a pitch Ph". The number of thread entries/thread spirals can be combined with a number of cutting edges (cf. FIG. 4, 5a, 5b, 5c, 5d) so that symmetrical or balanced forces are obtained, i.e. the forces balance each other out. Compare also with the above.

As has been stated above, the insertion time can be shortened in the case of implants which are designed with multiple thread entries. Of course, a shortened fitting time also reduces the expensive operating time, especially when fitting long and numerous implants. For example, when fitting six implants measuring 18 mm in length, which is not unusual in a so-called whole-jaw operation, 5 minutes of operating time are saved if two thread entries are used instead of one. Moreover, if the hole needs to be pre-threaded, then the saving in time is threefold.

Figure 13:
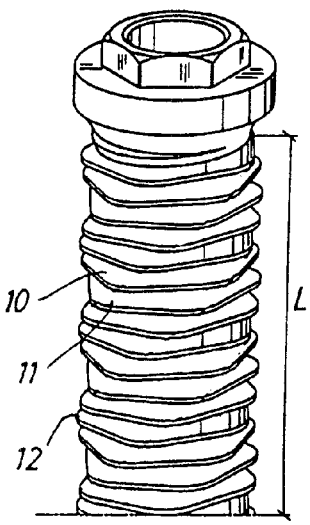
FIG. 13 shows, in a perspective view, the peripherally displaced non-circularity between different thread turns.

FIG. 13 shows an embodiment of the implant in which the non-circularity of the various thread cross-sections is displaced along the longitudinal direction L of the implant. Each thread 10 is displaced in relation to the adjacent thread 11 in the direction of rotation. The abovementioned bevelled corners are in this case indicated by 12. The wobble freedom on insertion of the implant into the hole in the bone with an instrument can in this way be further increased, i.e. improved rotational stability is obtained. Fitting is quicker and simpler. In addition, it is possible to use small initially cutting thread cutters to permit maximum thread area in the healing-in process. Some of the abovementioned embodiments can be used as soft-bone fixtures (cf. alternatives a) and b)). The invention can also be used in cases where the fitting is to be done with the aid of thread taps (i.e. in two stages).

Figure 14:
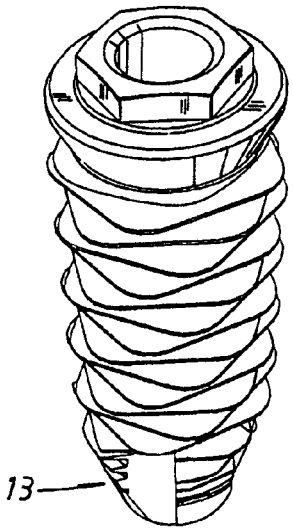
FIG. 14 shows, in a perspective view seen from above, a complete design according to FIG. 13.
Figure 15:
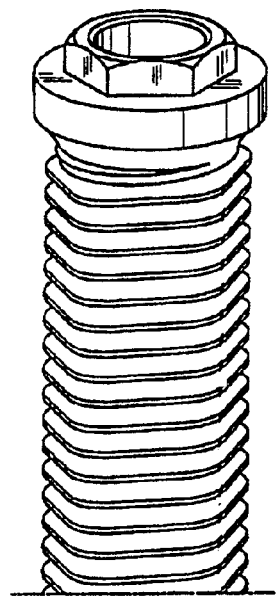
FIG. 15 shows, in a perspective view seen from above, an embodiment with non-circularity and no peripheral displacement thereof.

FIG. 14 shows a complete implant with displaced non-circularity according to FIG. 13 and a threaded tip part 13. FIG. 15 shows an illustrative embodiment in which the non-circularity between the different thread turns is not displaced.

Figure 16:
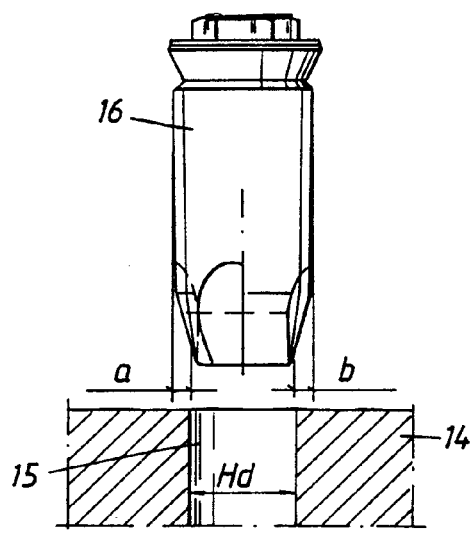
FIG. 16 shows, from the side, and in partial vertical section, an implant screw in relation to the hole in the dentine.

FIG. 16 shows the relationship for the chosen slight conicity and the hole diameter Hd for a hole 15 drilled in the dentine 14. With the hole diameter Hd=3 mm, the chosen values a and b for the conicity of the body 16 can be about 0.55 mm and 0.45 mm, respectively. The constant or essentially constant mutual pressures (cf. P and P') can be achieved in this way.

The conicity can be obtained either by means of the diameter of the whole thread profile gradually increasing as seen from the tip, or by means of the bottom diameter of the thread or its external diameter gradually increasing.

Figure 17:
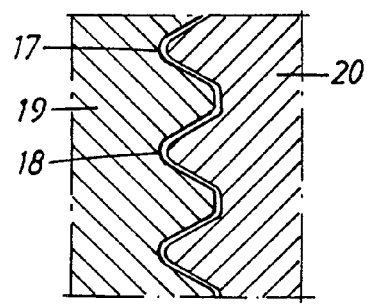
FIG. 17 shows, in vertical section, a concrete example of the thread arrangement.

FIG. 17 shows a concrete threading 17, 18 in the dentine 19 with the aid of the fixture 20.

Figure 18:
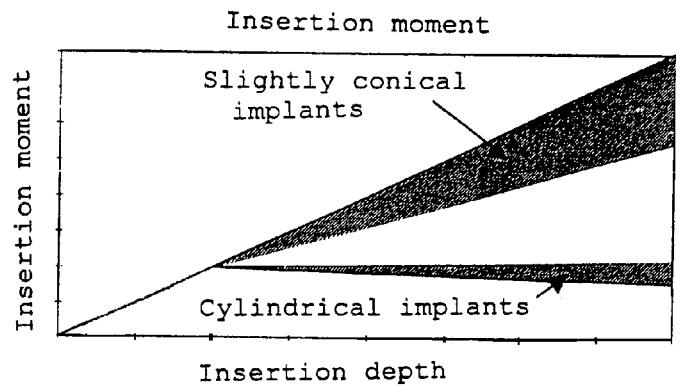
FIG. 18 shows a diagram of the insertion moment as a function of the insertion depth for two types of implants.

FIG. 18 shows the insertion moment as a function of the insertion depth, on the one hand for slightly conical implants and on the other hand for cylindrical implants. Since the pressure does not decrease during the insertion procedure and acts on an increasingly greater area of the implant, this means that the slightly conical implant requires an increasingly greater insertion moment, as can be seen from the figure. The greater insertion moment is a measure of the increased stability of the implant. Cylindrical implants have insertion curves with a constant or even decreasing moment, especially in the case of poor bone quality, as can also be seen from FIG. 18.

The invention is not limited to the embodiment shown above by way of example, but can be modified within the scope of the attached patent claims and the inventive concept.

The invention claimed is:

1. Threaded implant for obtaining reliable anchoring in bone substance, the bone substance being provided with a hole in whose side wall an internal threading may be established which can cooperate with an external threading on the implant for reliable anchoring and healing-in of the implant in the bone substance, wherein the implant threading is arranged to force the bone substance out in essentially radial directions as a function of the extent to which the implant is screwed into the hole, that the implant threading has a slight conicity which extends along most or part of the length of the implant and which cooperates with a circular cylindrical hole in the bone substance to effect greater forcing out of the bone substance at the outer parts of the hole than at the inner parts of the hole, the degree of forcing out being adapted in relation to the softness of the bone substance in order to achieve the reliable anchoring, and that said conical threading of the threading having the slight conicity comprises two or more thread spirals which provide a tight threading which permits effective integration with the bone substance during the healing-in process and counteracts deformation or breaking-up of fine bone trabeculae which surround the hole in the bone, wherein a tip portion of the implant is designed with a conical thread which has a conicity exceeding the conicity of the threading having the slight conicity, and wherein the tip portion of the implant has a length or height of about 10-30% of the length of the threaded part of the implant.

2. Implant according to claim 1, wherein the implant threading has a gradually increasing diameter as seen from the tip portion of the implant to ensure that the pressure between the bone substance and the implant has essentially a constant or slightly increasing value during the greater part of the operation of screwing the implant into the hole.

3. Implant according to claim 1, wherein the conicity of the slightly conical thread is chosen between 0.1-0.4 mm or has an angle of inclination of about 0.5-2°, and/or the thread conicity of the thread at the said tip portion of the implant is of the order of 0.4-0.8 mm or with an angle of inclination of about 10-15°.

4. Implant according to claim 1, wherein the implant threading along at least part of the longitudinal direction of the implant is given a noncircular or eccentric configuration for the purpose of obtaining improved rotational stability of the implant in the recently inserted state or the incorporated state of the implant in the bone substance.

5. Implant according to claim 4, wherein the implant is arranged with a minimum diameter which corresponds to or is slightly greater than the diameter of the hole in the bone substance.

6. Implant according to claim 4, wherein the implant is arranged with a minimum diameter that is 1-5% greater than the diameter of the hole in the bone substance.

7. Implant according to claim 1, wherein the tip portion of the implant has a circular or concentric thread which merges gradually into a non-circular or eccentric thread on the remaining part or parts of the implant.

8. Implant according to claim 7, wherein the peripheries of the different non-circular or eccentric thread cross-sections have bevelled corners.

9. Implant according to claim 7, wherein the non-circularity is arranged such that areas of maximum diameter are displaced in the peripheral direction from one thread turn to the next thread turn.

10. Implant according to claim 1, wherein the number of thread spirals of the threading having the slight conicity is two, three or four.

11. Implant according to claim 1, wherein the bone substance is a jaw-bone.

12. Implant according to claim 1, wherein the bone substance is soft.

13. Threaded implant for obtaining reliable anchoring in bone substance, the bone substance being provided with a hole in whose side wall an internal threading may be established which can cooperate with an external threading on the implant for reliable anchoring and healing-in of the implant in the bone substance, wherein the implant threading is arranged to force the bone substance out in essentially radial directions as a function of the extent to which the implant is screwed into the hole, that the implant threading has a slight conicity which extends along most or part of the length of the implant and which cooperates with a circular cylindrical hole in the bone substance to effect greater forcing out of the bone substance at the outer parts of the hole than at the inner parts of the hole, the degree of forcing out being adapted in relation to the softness of the bone substance in order to achieve the reliable anchoring, and that said conical threading of the threading having the slight conicity comprises two or more thread spirals which provide a tight threading which permits effective integration with the bone substance during the healing-in process and counteracts deformation or breaking-up of fine bone trabeculae which surround the hole in the bone, wherein four thread spirals are arranged together with four cutting edges,
  wherein a tip portion of the implant is designed with a conical thread which has a conicity exceeding the conicity of the threading having the slight conicity, and
  wherein the tip portion of the implant has a length or height of about 10-30% of the length of the threaded part of the implant.

* * * * *